United States Patent [19]

Bergstrand et al.

[11] Patent Number: 5,883,126
[45] Date of Patent: Mar. 16, 1999

[54] PHARMACOLOGICAL USE OF CERTAIN CYSTINE DERIVATIVES

[75] Inventors: Håkan Bergstrand, Bjärred; Knut Pettersson, Göteborg; Christer Westerlund, Mölndal, all of Sweden

[73] Assignee: Astra Aktiebolag, Sodertalje, Sweden

[21] Appl. No.: 619,681

[22] PCT Filed: Mar. 12, 1996

[86] PCT No.: PCT/SE96/00320

§ 371 Date: Mar. 29, 1996

§ 102(e) Date: Mar. 29, 1996

[87] PCT Pub. No.: WO96/28149

PCT Pub. Date: Sep. 19, 1996

[30] Foreign Application Priority Data

Mar. 14, 1995 [SE] Sweden .................................. 9500897

[51] Int. Cl.⁶ ........................ A61K 31/225; A61K 31/195
[52] U.S. Cl. ............................................ 514/547; 514/562
[58] Field of Search .................................... 514/255, 554, 514/562, 547

[56] References Cited

U.S. PATENT DOCUMENTS

| | | |
|---|---|---|
| 3,878,305 | 4/1975 | Damico et al. . |
| 3,952,115 | 4/1976 | Damico et al. . |
| 4,708,965 | 11/1987 | Morgan . |
| 4,724,239 | 2/1988 | Morgan . |
| 4,827,016 | 5/1989 | Morgan . |
| 5,254,579 | 10/1993 | Poli et al. . |
| 5,385,904 | 1/1995 | Andersson et al. . |
| 5,650,538 | 7/1997 | Jakupovic et al. . |

FOREIGN PATENT DOCUMENTS

| | | |
|---|---|---|
| 0300100 | 1/1989 | European Pat. Off. . |
| 0463514 | 1/1992 | European Pat. Off. . |
| 8.205M | 9/1970 | France . |
| 2503151 | 4/1981 | France . |
| 2326444 | 12/1973 | Germany . |
| 62-195356 | 8/1987 | Japan . |
| 1468646 | 3/1977 | United Kingdom . |
| 2097256 | 11/1982 | United Kingdom . |
| 9118594 | 12/1991 | WIPO . |
| 9313660 | 7/1993 | WIPO . |
| 9402128 | 2/1994 | WIPO . |

OTHER PUBLICATIONS

Stevenson, F.K. "Tumor Vaccines," FASEB 5: 2250–2257.
Rosenberg, S.A. "Immunotherapy of Cancer using Interleukin 2: Current Status and Future Prospects," Immunology Today 9: 58–62, 1988.
Scully et al. "Weekly Clinicopathological Exercises," The New England Journal of Medicine 322: 252–261, 1990.
Roitt et al. "Hypersensitivity–Type IV," Immunology 22.1–22.9., Churchill Livingston eds. Grover Med. Pub., London, N.Y.
Varela et al. "Second Generation Immune Networks," Immunology Today 12: 159–166, 1991.
Hadden, John W. "Immunotherapy of Human Immunodeficiency virus Infection," TIPS Reviews 12: 107–111, 1991.
Radermecker et al. "Increase in the Number and the Phagocytic Function of Guinea Pig Pulmonary and Peritoneal Macrophages Following Oral Administration of RU 41740, A Glycoprotein Extract from Klebsiella Pneumoniae," J. Immunopharmac 10: 913–917, 1988.
Paupe, Jean. "Immunotherapy with an Oral Bacterial Extract (OM–85 BV) for Upper Respiratory Infection," Respiration 58: 150–154, 1991.
Sjodin et al. "Metabolism of N–Acetyl–L–Cysteine," Biochemical Pharmacology 38: 3981–3985, 1989.
Anderson et al. "TH2 and 'TH2–like' Cells in Allergy and Asthma: Pharmacological Perspectives," Tips 15: (1980) 324–332.
Katz, David H. "The Allergic Phenotype: Manifestation of 'Allergic Breakthrough' and Imbalance in Normal 'Damping' of IgE Antibody Production," Immunological Rev. 41: 77–108, 1978.
Bergstrand et al. "Stimuli–induced Superoxide Radical Generation in Vitro by Human Alveolar Macrophages from Smokers: Modulation by N–Acetylcysteine Treatment in Vivo," Journal of Free Radicals in Biology & Medicine 2: 119–127, 1986.
Van Wauwe et al. "Review Article: On the Biochemical Mode of Action of Levamisole: an Update," J. Immunopharmac. 13: 3–9, 1991.
Kahns et al. "Prodrugs as Drug Delivery Systems. 107. Synthesis and Chemical and Enzymatic Hydrolysis Kinetics of Various Mono– and Diester Prodrugs of N–acetylcysteine," International Journal of Pharmaceutics 62: 193–205, 1990.
Schaad et al. "Linear Regression Analysis of Inhibitory Potency of Organic Disulfides against Histoplasma Capsulatum," Journal of Medicinal Chemistry 18: 344–351, 1975.
Martin, Tellis A. "N–Acyl– and N–Sulfonylcysteine Derivatives," Journal of Medicinal Chemistry 12: 950–953, 1969.
Scheffer et al. "Effect of an Immunostimulatory Substance of Klebsiella Pneumoniae on Inflammatroy Responses of Human Granulocytes, Basophils and Platelets," Arzneim–Forsch Drug Res. 41: 815–820, 1991.
Akenase, Philip W. "Delayed–Type Hypersensitivity Recruitment of T Cell Subsets via Antigen–Specific Non–IgE Factors or IgE Antibodies: Relevance to Asthma, Autoimmunity," Chem. Immunol. 54: 166–211, 1992.
Kemp et al. "Templates for Intramolecular O,N–Acyl Transfer via cyclic Intermediates Derived from Mercury Derivatives of L–Cysteine: Progress toward a Mercury–Based Thiol Capture Strategy," J. Org. Chem. 54: 3853–3858, 1989.
Bowman et al. "Reactions of Thiolate Anions with 2–Substituted–2–Nitropropanes," Tetrahedro Letters 22: 1551–1554, 1981.
Devlin, Thomas M. "Lipid Metabolism I: Utilization and Storage of Energy in Lipid Form," Biochemistry Correlations 482–484, 1982.

*Primary Examiner*—Raymond Henley, III
*Attorney, Agent, or Firm*—White & Case LLP

[57] ABSTRACT

A method for the treatment of restenosis using certain cystine derivatives and a pharmaceutical preparation comprising these derivatives.

4 Claims, No Drawings

PHARMACOLOGICAL USE OF CERTAIN CYSTINE DERIVATIVES

This is a 371 of PCT/SE96/00320 filed Mar. 12, 1996.

FIELD OF THE INVENTION

The present invention relates to a new medical use of a certain cystine derivatives.

In particular the invention relates to the use of such cystine derivatives for the preparation of medicaments with effect against restenosis.

BACKGROUND OF THE INVENTION

Such cystine derivatives as to which the present invention has found a new pharmacological use are known from WO 91/185 94 and EP 463 514 to have immunomodulating activity. Nothing is reported or generally known concerning the pharmacological and/or therapeutic properties of these compounds with respect to effects or restenosis.

In connection with the present invention compounds of the general formula I are employed:

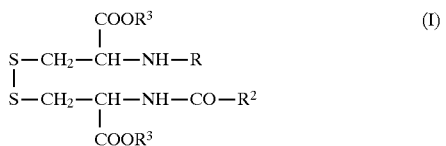

wherein R is hydrogen, methyl, ethyl, n-propyl or a moiety -COR$^1$, wherein R$^1$ is a straight or branched akyl group having 1–12 carbon atoms, R$^2$ is a straight or branched alkyl group having 1–12 carbon atoms and R$^3$ is a moiety which provides an ester hydrolysable in body fluids to release the active compound in free acid form, or a physiologically acceptable salt and/or a stereochemical isomer thereof.

In particular compounds of the formula I wherein R is hydrogen or a moiety -CO-R$^1$ wherein R$^1$ is methyl, ethyl, n-propyl, n-butyl, n-pentyl, n-hexyl, n-heptyl, n-octyl, n-nonyl, n-decyl, n-undecyl, isopropyl, 1-methylpropyl, 2-methylpropyl, tert. butyl, 3-methylbutyl or 2-metylbutyl, R$^2$ is methyl, ethyl, n-propyl, n-butyl, n-pentyl, n-hexyl, n-heptyl, n-octyl, n-nonyl, n-decyl, n-undecyl, isopropyl, 1-methylpropyl, 2-methylpropyl, tert. butyl, 3-methylbutyl or 2-methylbutyl and R$^3$ is hydrogen, methyl, ethyl, propyl, isopropyl, butyl or isobutyl, or a physiologically acceptable salt and/or a stereochemical isomer thereof, are preferred.

The compounds of formula I are used in racemic form as well as stereoisomers (enantiomers, diastereomers). Of particular interest are the compounds having the L configuration, particularly interesting is N,N'-diacetyl-L-cystine.

The invention also involves the compound of formula I in the form of its physiologically acceptable salts, such as the salts of sodium, potassium, ammonium, calcium or magnesium. Also included are salts of the unesterified compounds with pharmaceutically acceptable organic bases, such as lysine, ethylenediamine, N,N'-dibenzylethylenediamine, adamantanamine, N-benzyl-2-phenylethylamine and piperazine.

Lysine and arginine can be used in its D- or L- forms. Most preferred is the L-form.

The most preferred compound is di-L-lysinium-N,N'-diacetyl-L-cystinate (compound A).

The compounds of the general formula I may be prepared by any of the processes disclosed in EP 463 514. Salts of such compounds with organic bases are prepared according to any conventional method or any method disclosed in WO 93/11104.

PRIOR ART

Rapid development of the tunica intima occurs following mechanical injury to arteries. The most common such complication is the so called restenosis that occurs after percutaneous transluminal coronary angioplasty (PTCA), i.e. the removal of arteriosclerotic lesions causing stenosis in coronary vessels wih a balloon catheter, but similar complications can occur also as a result of other procedures and interventions.

After PTCA, restenosis develops in all patients. In approximately ⅓ of the patients, this consequence is so severe that within 3 to 6 months the developed restenosis requires renewed PTCA or coronary by-pass surgery. The need for chemotherapy that can substantially reduce the incidence of severe restenosis is thus obvious.

Acute thrombosis is a distinct risk during angioplastic manoeuvres, and heparin is therefore given during the surgical treatment. For the same reason aspirin is usually given for a period of time after the treatment. However,this medication does not reduce the development of restenosis in the months following the PTCA. Thus, there is today no generally accepted treatment available which reduces sufficiently the incidence of restenosis. However, recently published clinical trials have shown that the antiplatelet agent trapedil (Maresta et al, Circulation 1994;90:2710–15) and the hypolipidemic (and antioxidant) probucol (Setsuda et al, Clin Ther 1993; 15:174–82) can at least partly prevent the development of restenosis.

The current possibilities to prevent restenosis are still inadequate, and can also be associated with unwanted side effects, such as increased bleeding risk following aspirin and trapedil treatment.

DISCLOSURE OF THE INVENTION

It has unexpectedly been found that compounds of the general formula

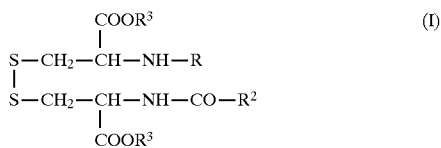

wherein R is hydrogen, methyl, ethyl, n-propyl or a moiety -COR$^1$, wherein R$^1$ is straight or branched alkyl group having 1–12 carbon atoms, R$^2$ is a straight or branched alkyl group having 1–12 carbon atoms and R$^3$ is a moiety which provides an ester hydrolysable in body fluids to release the active compound in free acid form, or a physiologically acceptable salt and/or a stereochemical isomer thereof are potent in an experimental animal model for assessing restenosis.

In particular the compounds of formula I wherein R is hydrogen or a moiety -CO-R$^1$ wherein R$^1$ is methyl, ethyl, n-propyl, n-butyl, n-pentyl, n-hexyl, n-heptyl, n-octyl, n-nonyl, n-decyl, n-undecyl, isopropyl, 1-methylpropyl, 2-methylpropyl, tert. butyl, 3-methylbutyl or 2-methylbutyl, R$^2$ is methyl, ethyl, n-propyl, n-butyl, n-petnyl, n-hexyl, n-heptyl, n-octyl, n-nonyl, n-decyl, n-undecyl, isopropyl, 1-methylpropyl, 2-methylpropyl, tert. butyl, 3-methylbutyl or 2-methylbutyl and R$^3$ is hydrogen, methyl, ethyl, propyl, isopropyl, butyl or isobutyl, or a physiologically acceptable salt and/or a stereochemical isomer thereof are of interest.

Therefore, the compounds of the general formula I, their stereoisomers (enantiomers, diastereomers) and salts thereof may be used for the prophylaxis or treatment of restenosis.

Accordingly, the invention includes the use of these compounds for the preparation of a medicament for prophylaxis or treatment of restenosis. The invention also includes a method for the prophylaxis or treatment of restenosis using compounds of formula I.

Effects of compounds in experimental models of restenosis.

The most commonly used animal model of restenosis is rat carotid arteries or aortas that have been dilated with balloon catheters. For this purpose, rats were anaesthetized, and the carotid bifurcation was exposed surgically. A balloon catheter (a 2F Fogarty catheter) was introduced from the bifurcation to the aorta, inflated and withdrawn. This procedure leads to the development of a "neointima" with a microscopic appearance similar to that of restenosis in humans.

The active compounds were administered as a solution in the drinking water in doses corresponding to 0.003–30 $\mu$moles/kg/day for 2–4 weeks. The extent of the cross-section area of neointima and the media was evaluated microscopically 2 to 4 weeks after denudation. At termination of the studies, the rats were therefore perfusion-fixed and microscopic specimens from the carotid arteries were produced, and the cross-section areas were obtained through morphometric procedures using point-counting and/or cutting out and weighing photos of the neointima and media.

Initial studies were performed in Sprague-Dawley rats. Neointima formation was dependent on a sufficient response in the media layer, and proportional to the media area when this exceeded a certain threshold value. The results are therefore expressed as the neointima-to-media ratio. Doses from 0.03 to 3.0 $\mu$moles/kg/day could reduce the neointima/media ratio by more than 20%.

Pharmaceutical formulations

The described active substances for human use can be prepared in different dosage forms e.g. tablets, coated tablets, gelatin capsules, oral solutions, solutions for injection, and aerosols and dry powder for inhalation.

For the preparation of tablets, coated tablets and gelatin capsules the active substances can be combined with pharmaceutically acceptable carriers or diluents, e.g. lactose, starch, dicalcium phosphate, microcrystalline cellulose, polyvinylpyrrolidone, gelatin, cellulose derivatives, colloidal silicone dioxide, talc and stearic acid or its salts.

For the preparation of oral solutions suitable excipients are water or solutions of saccharose, glucose, sorbitol, fructose or zylitol.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are conveniently dispensed into unit doses in the form of ampoules or vials. Solutions for parenteral administration may also be prepared as a dry preparation to be reconstituted with a suitable solvent extemporaneously before use.

The substance can be inhaled from a pressurized metered dose inhaler, from a dry powder inhaler, e.g. a Turbuhaler® or from a dry powder inhaler utilizing gelatine, plastic or other capsules. Non-toxic and chemically inert substances e.g. lactose, trehalose, mannitol or glucose can be added to the powdered substance for inhalation therapy.

Pressurized aerosols are intended for oral or nasal inhalation. The aerosol system is generally designed in such a way that each delivered dose contains 10–1000 $\mu$g, preferably 20–250 $\mu$g of the active compound. The most active compounds are administered in the lower part of the dose range. For inhalation therapy micronized compound are used and there consists of particles substantially smaller than 5 $\mu$m, which are suspended in a propellant mixture with the assistance of a dispersant, such as sorbitan trioleate, oleic acid, lecithin or sodium salt of dioctylsulphosuccinic acid.

The dosage forms can contain in addition to mentioned excipients preservatives, stabilizers, viscosity regulating agents, emulsifiers, sweetening agents, colouring agents, flavouring agents, tonicity regulating agents, buffers or antioxidants. They can also contain other therapeutically valuable substances.

The compounds of the formula I will normally be administered orally, rectally, by injection or inhalation, in the form of pharmaceutical preparations comprising the active ingredient either as the compound per se or as a pharmaceutically acceptable non-toxic, acid addition salt. The dosage form may be a solid, semisolid or liquid preparation. Usually the active substance will constitute between 0.1 and 99% by weight of the preparation, more usually between 0.5 and 20% by weight for preparations for injection and between 0.2 and 50% by weight for preparations for oral administration.

Effective amounts of the compounds of the formula I for use in the prophylaxis and treatment of restenosis are in the range 0.5–500 mg, preferably 1–100 mg for a daily dose.

The following examples illustrate medicaments for prophylaxis or treatment of restenosis.

EXAMPLE 1

Tablet containing 10 mg of compound A per tablet:

Compound A 10 mg

Lactose 100 mg

Potato starch 50 mg

Polyvinylpyrrolidone 5 mg

Microcrystalline cellulose 15 mg

Magnesium sterate 1 mg

EXAMPLE 2

Direct compression tablet containing 5 mg of compound A per tablet:

Compound A 5 mg

Lactose, anhydrous 150 mg

Microcrystalline cellulose 50 mg

Colloidal silicon dioxide 1 mg

Magnesium sterate 2 mg

If desired, the obtained tablets can be film coated with e.g. hydroxypropyl methylcellulose, hydroxypropyl cellulose or dimethylaminoethyl methacrylate methacrylic acid ester copolymer.

EXAMPLE 3

Solution for injection containing compound A 1 mg/ml

Compound A 1.0 mg

Sodium chloride 8.8 mg

Water for injection to 1 ml

EXAMPLE 4

Oral solution containing Compound A 1 mg/ml

Compound A 1.0 mg

Sorbitol 150 mg

Glycering 100 mg

Disodium edetate 0.5 mg

Preservative q.s.
Flavour q.s.
Water, purified to 1 ml

EXAMPLE 5

Powder aerosol giving 1 mg compound A per dose

The micronized compound A can be filled into a powder inhaler device e.g. Turbuhaler® giving 1 mg/dose.

EXAMPLE 6

Presurised aerosol for inhalation

The aerosol system is arranged so that each metered dose contains 0.1–1.0 mg.
Compound A, micronized 1.0 % w/w
Sorbitan trioleate 0.7 % w/w
Trichloromonofluoromethane 24.4 % w/w
Dichlorotetrafluoroethane 24.4 % w/w
Dichlorodifluoromethane 49.5 % w/w

EXAMPLE 7

Powder aerosol for inhalation of pure substance
Pure substance prepared for inhalation from Turbuhaler.
Each single dose contains 0.1–1.0 mg.
Compound A, processed 0.1–1.0 mg

EXAMPLE 8

Powder aerosol for inhalation
Each single dose contains 0.1–1.0 mg in a capsule.
Compound A, micronized 0.1–1.0 mg
Lactose 50 mg

EXAMPLE 9

Solution for nebulising
The solution contains 1.0–10.0 mg/mL and 1–3 mL may be administered in a single dose.
Compound A 1.0–10.0 mg
Water for injection to 1.0 mL

EXAMPLE 10

Tablets
Each tablet contains:
Compound A 0.1–100 mg
Maize starch 50 mg
Lactose 150 mg
Polyvidone 7 mg
Microcrystalline cellulose 20 mg
Magnesium stearate 2 mg

EXAMPLE 11

Oral solution
A single dose of 10 mL contains 10–100 mg.
Compound A 1–10 mg
Sorbitol 70% 150 mg
Glycerol 100 mg
Sodium benzoate 1 mg
Flavour q.s.
Water purified to 1.0 mL

EXAMPLE 12

Tablet for controlled release
1 tablet:
Compound A 1–100 mg
Paraffin Special 145 mg
Lactose Powder 50 mg
Colloidal Silicon Dioxide 5 mg
Ethylcellulose 10 cps 13 mg
Ethanol 99,5 vol % 85 mg
Magnesium Stearate 2,5 mg

EXAMPLE 13

Granulate for controlled release
1 g of granulate:
Compound A 1–100 mg
Ethylcellulose Dispersion 10 mg
Acetyltributylcitrate 0.5 mg
Eudragit L 100-55 55 mg
Triethylcitrate 5 mg
Talc 30 mg
Water newly distilled 350 mg
Pellets, neutral to 1000 mg

EXAMPLE 14

Solution for injection
1 mL in a single dose contains 1.0–10.0 mg
Compound A 1.0–10.0 mg
Sodium chloride 8.9–7.7 mg
Water for injection to 1.0 mL

EXAMPLE 15

Cream for topical application
1 g of cream contains:
Compound A 0.1–1 mg
White soft paraffin 75 mg
Liquid paraffin 10 mg
Cetostearyl alcohol 75 mg
Cetomacrogol 1000 20 mg
Metagin 0.8 mg
Propagin 0.2 mg
Water, purified to 1.0 g

We claim:

1. A method for the prophylaxis or treatment of restenosis in mammals, which comprises the administration to a host in need of such prophylaxis or treatment of an effective amount of a compound of the formula I

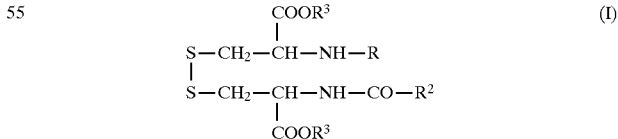

or a physiologically acceptable salt and/or stereochemical isomer thereof, wherein R is hydrogen, methyl, ethyl, n-propyl or a moiety -COR$^1$, wherein R$^1$ is a straight or branched alkyl group having 1–12 carbon atom;, R$^2$ is a straight or branched alkyl group having 1–12 carbon atoms; and R$^3$ is a moiety which provides an ester hydrolysable in body fluids to release the active compound in free acid form.

2. A method for the prophylaxis or treatment of restenosis in mammals, which comprises the administration to a host in need of such prophylaxis or treatment of an effective amount of a compound of the formula I

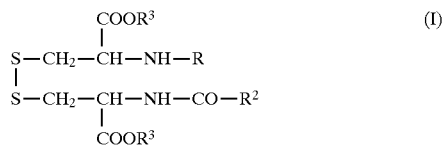
(I)

or a physiologically acceptable salt and/or stereochemical isomer thereof, wherein R is hydrogen or a moiety -CO-$R^1$ wherein $R^1$ is methyl, ethyl, n-propyl, n-butyl, n-pentyl, n-hexyl, n-heptyl, n-octyl, n-nonyl, n-decyl, n-undecyl, isopropyl, 1-methylpropyl, 2-methylpropyl, tert. butyl, 3-methylbutyl or 2-methylbutyl; $R^2$ is methyl, ethyl, n-propyl, n-butyl, n-pentyl, n-hexyl, n-heptyl, n-octyl, n-nonyl, n-decyl, n-undecyl, isopropyl, 1-methylpropyl, 2-methylpropyl, tert. butyl, 3-methylbutyl or 2-methylbutyl; and $R^3$ is hydrogen, methyl, ethyl, propyl, isopropyl, butyl or 2-methylpropyl.

3. A method according to claim 2 wherein the L isomer of N,N'-diacetylcystine or a physiologically acceptable salt thereof is administered.

4. A method according to claim 3 wherein di-L-lysinium-N,N'-diacetyl-L-cystinate is administered.

* * * * *